United States Patent
Li et al.

(10) Patent No.: US 11,819,356 B2
(45) Date of Patent: Nov. 21, 2023

(54) MULTI-SEQUENCE SCANNING METHODS AND APPARATUSES, DEVICES AND CT SYSTEMS

(71) Applicant: Neusoft Medical Systems Co., Ltd., Liaoning (CN)

(72) Inventors: Wei Li, Liaoning (CN); Jinjun Liu, Liaoning (CN)

(73) Assignee: Neusoft Medical Systems Co., Ltd., Shenyang (CN)

( * ) Notice: Subject to any disclaimer, the term of this patent is extended or adjusted under 35 U.S.C. 154(b) by 200 days.

(21) Appl. No.: 17/384,245

(22) Filed: Jul. 23, 2021

(65) Prior Publication Data
US 2022/0022837 A1 Jan. 27, 2022

(30) Foreign Application Priority Data
Jul. 24, 2020 (CN) .......................... 202010725654.6

(51) Int. Cl.
*A61B 6/00* (2006.01)
*G16H 30/20* (2018.01)
(Continued)

(52) U.S. Cl.
CPC .............. *A61B 6/545* (2013.01); *A61B 6/032* (2013.01); *G16H 30/20* (2018.01); *G16H 40/63* (2018.01)

(58) Field of Classification Search
CPC ........ G16H 40/63; G16H 30/20; G16H 20/40; G16H 50/50; G16H 30/40; G16H 50/30;
(Continued)

(56) References Cited

U.S. PATENT DOCUMENTS 8,126,109 B2 2/2012 Tsukagoshi
9,238,099 B2 * 1/2016 Kalafut ................. G16H 40/63
(Continued)

FOREIGN PATENT DOCUMENTS

| CN | 101502422 A | 8/2009 |
|----|-------------|--------|
| CN | 104434159 A | 3/2015 |
| CN | 108135551 A | 6/2018 |

OTHER PUBLICATIONS

Office Action in Chinese Appln. No. 2020107256546, dated Oct. 25, 2022, 18 pages. (Submitted with Machine/Partial Translation).
(Continued)

*Primary Examiner* — Irakli Kiknadze
(74) *Attorney, Agent, or Firm* — Fish & Richardson P.C.

(57) ABSTRACT

Multi-sequence scanning methods and apparatuses, devices and CT systems are described. A multi-sequence scanning method may include: in response to a parameter configuration command, configuring scan sequence parameters for a plurality of scan sequences in a scan protocol to obtain a target scan protocol, where the scan sequence parameters include a scan start time and a scan duration of each of the scan sequences, and a scan switching duration between the scan sequences, where a total scan duration of the scan sequences in the target scan protocol is configured to be less than or equal to a preset total scan duration, and where the scan switching duration between the scan sequences is configured in a shortest duration mode; and in response to receiving a scan command, controlling the CT system to scan a scanned object according to the scan sequence parameters configured in the target scan protocol.

18 Claims, 6 Drawing Sheets

(51) Int. Cl.
*G16H 40/63* (2018.01)
*A61B 6/03* (2006.01)

(58) Field of Classification Search
CPC ........... A61B 6/032; A61B 6/54; A61B 6/545;
A61B 6/481; A61B 6/501; A61B 6/507;
A61B 6/5217; A61B 6/542; A61B 6/467;
A61B 6/461; A61B 6/469; A61B 6/468;
A61B 6/482; A61B 6/504; A61B 6/465;
A61B 6/4241; A61B 6/037; A61B
5/0275; A61B 5/0263; A61B 6/488; A61B
8/481; A61B 6/541; A61B 5/055; A61B
8/5223; A61B 6/463; A61B 6/4208; A61B
6/486; A61B 6/5205; A61B 6/484; A61B
5/7264; A61B 6/42; A61B 6/0407; A61B
6/40; G06N 20/00; G06N 3/04; A61M
5/007; G01R 33/5673; G01R 33/4814;
G06F 3/0482; G06F 3/04847; G06T
7/0016; G06T 7/11
USPC ................................................ 378/4, 18, 62
See application file for complete search history.

(56) References Cited

U.S. PATENT DOCUMENTS

| | | | |
|---|---|---|---|
| 10,383,590 B2 | 8/2019 | Vaz et al. | |
| 2008/0119715 A1* | 5/2008 | Gonzalez Molezzi | ..................... A61B 6/481 600/407 |
| 2009/0245459 A1* | 10/2009 | Goto | ....................... A61B 6/032 378/116 |
| 2010/0292570 A1* | 11/2010 | Tsukagoshi | ............ A61B 6/481 600/431 |
| 2014/0257094 A1 | 9/2014 | Meetz et al. | |
| 2016/0091585 A1 | 3/2016 | Benner et al. | |

OTHER PUBLICATIONS

Office Action in Chinese Appln. No. 2020107256546, dated Mar. 25, 2023, 16 pages (Submitted with Machine Translation).

\* cited by examiner

MULTI-SEQUENCE SCANNING METHODS AND APPARATUSES, DEVICES AND CT SYSTEMS

CROSS-REFERENCE TO RELATED APPLICATIONS

The present disclosure claims priority to Chinese patent application No. 202010725654.6 filed on Jul. 24, 2020, and entitled "MULTI-SEQUENCE SCANNING METHODS AND APPARATUSES, DEVICES AND CT SYSTEMS", which is incorporated herein by reference in its entirety.

TECHNICAL FIELD

The present disclosure relates to the field of CT (Computed Tomography) technology, and in particular to a multi-sequence scanning method and apparatus, a device, and a CT system.

BACKGROUND

Multi-sequence scanning is a common CT scanning method. For example, in a stroke examination, a combined CTP-CTA scan may be performed on head and neck, where blood perfusion of brain tissues may be checked by scanning with a CTP (CT Perfusion) scan sequence, and arteries of the head and neck may be checked by scanning with a CTA (CT Angiography) scan sequence, so as to more clearly determine a degree of vascular stenosis and a decrease in blood flow in related brain tissues.

SUMMARY

The present disclosure provides a multi-sequence scanning method and apparatus, a device, and a CT system.

In a first aspect, the present disclosure provides a multi-sequence scanning method, including: in response to a parameter configuration command, configuring scan sequence parameters for a plurality of scan sequences in a scan protocol to obtain a target scan protocol, where the scan sequence parameters include a scan start time and a scan duration of each of the scan sequences, and a scan switching duration between the scan sequences, where a total scan duration of the scan sequences in the target scan protocol is configured to be less than or equal to a preset total scan duration, and where the scan switching duration between the scan sequences is configured in a shortest duration mode; and in response to receiving a scan command, controlling the CT system to scan a scanned object according to the scan sequence parameters configured in the target scan protocol.

In a second aspect, the present disclosure provides an electronic device, including:

at least one processor; and one or more memories coupled to the at least one processor and storing programming instructions for execution by the at least one processor to perform operations including:

in response to a parameter configuration command, configuring scan sequence parameters for a plurality of scan sequences in a scan protocol to obtain a target scan protocol, where the scan sequence parameters include a scan start time and a scan duration of each of the scan sequences, and a scan switching duration between the scan sequences, where a total scan duration of the scan sequences in the target scan protocol is configured to be less than or equal to a preset total scan duration, and where the scan switching duration between the scan sequences is configured in a shortest duration mode; and in response to receiving a scan command, controlling the CT system to scan a scanned object according to the scan sequence parameters configured in the target scan protocol.

In a third aspect, the present disclosure provides a CT system, including a ray source, a detector and an electronic device, where the ray source is configured to emit rays; the detector is configured to detect an attenuated ray signal after the rays pass through a scanned object, and convert the attenuated ray signal into an electrical signal which is sent to the electronic device; and the electronic device is configured to: in response to a parameter configuration command, configure scan sequence parameters for a plurality of scan sequences in a scan protocol to obtain a target scan protocol, where the scan sequence parameters include a scan start time and a scan duration of each of the scan sequences, and a scan switching duration between the scan sequences, where a total scan duration of the scan sequences in the target scan protocol is configured to be less than or equal to a preset total scan duration, and where the scan switching duration between the scan sequences is configured in a shortest duration mode; and in response to receiving a scan command, control the CT system to scan the scanned object according to the scan sequence parameters configured in the target scan protocol.

In a fourth aspect, the present disclosure provides a non-transitory computer-readable storage medium coupled to at least one processor and storing programming instructions for execution by the at least one processor to perform the method according to the first aspect.

As above, scan sequence parameters may be automatically configured for a scan protocol in response to a parameter configuration command to obtain a target scan protocol, and then in response to receiving a scan command, a CT system may be controlled to scan a scanned object according to the scan sequence parameters configured in the target scan protocol. There is no need to manually set the parameters for each scan sequence. Instead, parameter setting of multi-sequence scanning is automated, reducing the risk of misoperation during the multi-sequence scanning, and improving the efficiency of the multi-sequence scanning.

Embodiments of any of the first through fourth aspects can include one or any combination of two or more of the following features.

Configuring the scan sequence parameters for the plurality of scan sequences in the scan protocol includes monitoring a scan peak time, where the scan peak time is the time when an average of CT values of a region of interest reaches a preset threshold, and the region of interest is a preset region where the CT values are to be monitored; and configuring the scan start time of the scan sequence covering the scan peak time according to the monitored scan peak time, such that the scan start time of the scan sequence is earlier than or concurrent with the scan peak time.

The scan sequences include a first scan sequence and a second scan sequence, and the first scan sequence is a previous scan sequence of the second scan sequence. Configuring the scan sequence parameters for the plurality of scan sequences in the scan protocol includes monitoring a scan peak time, where the scan peak time is the time when an average of CT values of a region of interest reaches a preset threshold, and the region of interest is a preset region where the CT values are to be monitored; configuring the scan start time of the second scan sequence according to the monitored scan peak time, such that the scan start time of the second scan sequence is earlier than or concurrent with the scan peak time; and adjusting the scan sequence parameters of the first scan sequence such that the time between the scan start time of the first scan sequence and the scan start time of the second scan sequence is equal to a sum of the scan duration of the first scan sequence and the scan switching duration, where the scan switching duration is the time to switch from the first scan sequence to the second scan sequence.

Adjusting the scan sequence parameters of the first scan sequence includes adjusting the scan duration of the first scan sequence by adjusting a number of scan circles for the first scan sequence, a scan duration per scan circle for the first scan sequence, or both.

When the first scan sequence is the first one of the scan sequences, adjusting the scan sequence parameters of the first scan sequence includes at least one of adjusting the scan start time of the first scan sequence; or adjusting the scan duration of the first scan sequence by adjusting a number of scan circles for the first scan sequence, a scan duration per scan circle for the first scan sequence, or both.

Adjusting the scan sequence parameters of the first scan sequence includes determining an actual scan end time of the first scan sequence according to an initial scan start time, an initial number of scan circles, and an initial scan duration per scan circle for the first scan sequence; obtaining a theoretical scan end time of the first scan sequence by subtracting the scan switching duration between the second scan sequence and the first scan sequence from the scan start time of the second scan sequence; and in response to the actual scan end time being inconsistent with the theoretical scan end time, adjusting the scan sequence parameters of the first scan sequence.

The scan sequences further include a third scan sequence, the third scan sequence is the next scan sequence of the second scan sequence, and the third scan sequence is the last one of the scan sequences. Configuring the scan sequence parameters for the plurality of scan sequences in the scan protocol includes adjusting scan sequence parameters of the third scan sequence such that the time between a scan end time of the third scan sequence and the scan start time of the first scan sequence is less than or equal to the preset total scan duration.

The parameter configuration command includes one or more system operating parameters to be adjusted and values of the system operating parameters. The method further includes, before configuring the scan sequence parameters for the plurality of scan sequences in the scan protocol, determining one or more target system operating parameters to be adjusted in synchronization with each of the system operating parameters to be adjusted, according to a parameter adjustment correlation and each of the system operating parameters to be adjusted, wherein the parameter adjustment correlation is configured to characterize a synchronous adjustment relationship between each of the system operating parameters to be adjusted and respective target system operating parameters; and adjusting values of the respective target system operating parameters according to the value of each of the system operating parameters to be adjusted.

Other features and advantages of the present disclosure will be described in detail in the following DETAILED DESCRIPTION.

BRIEF DESCRIPTION OF THE DRAWINGS

The accompanying drawings, which are intended to provide a further understanding of the present disclosure and constitute a part of the specification, are used to explain the present disclosure in conjunction with the following DETAILED DESCRIPTION, but do not constitute any limitation on the present disclosure.

DETAILED DESCRIPTION OF THE EMBODIMENTS

The DETAILED DESCRIPTION of the present disclosure will be described in detail below in conjunction with the accompanying drawings. It should be understood that the DETAILED DESCRIPTION described herein are merely used to illustrate and explain the present disclosure, and are not intended to limit the present disclosure.

Multi-sequence scanning is a common CT scanning method. For example, in a stroke examination, a combined CTP-CTA scan may be performed on head and neck, where blood perfusion of brain tissues may be checked by scanning with a CTP (CT Perfusion) scan sequence, and arteries of the head and neck may be checked by scanning with a CTA (CT Angiography) scan sequence, so as to more clearly determine a degree of vascular stenosis and a decrease in blood flow in related brain tissues.

Figure 1:
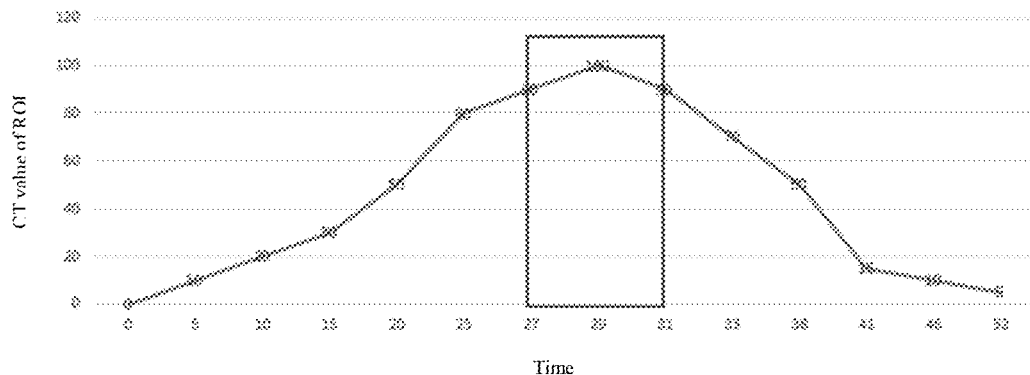
FIG. 1 is a graph illustrating CT values obtained during a test scan versus time.

In the related art, an operator generally manually sets a scan start time, a scan duration, and other parameters of each scan sequence during the multi-sequence scanning. For example, in a stroke examination, a combined CTP-CTA scan may be performed on the head and neck, with a CTP1 scan sequence, a CTA scan sequence, and a CTP2 scan sequence in that order. The operator may first inject a contrast agent into a scanned object to perform a test scan. After the test scan, a graph of CT values of a region of interest (ROI) versus time may be generated as shown in FIG. 1, where the ROI is a preset region where the CT values are to be monitored, and the CT values are used to characterize a density of a local tissue or an organ in a human body. Referring to FIG. 1, a portion marked with a box is a peak area for the CT values. The operator may record the start time of the peak area, and then determine the start time as the scan start time of the CTA scan sequence.

Figure 2:
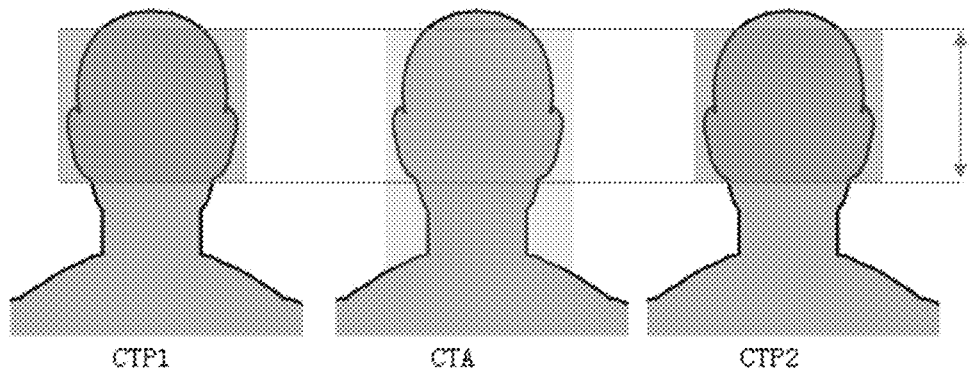
FIG. 2 is a schematic diagram illustrating a manual adjustment of scan ranges of scan sequences.
Figure 3:
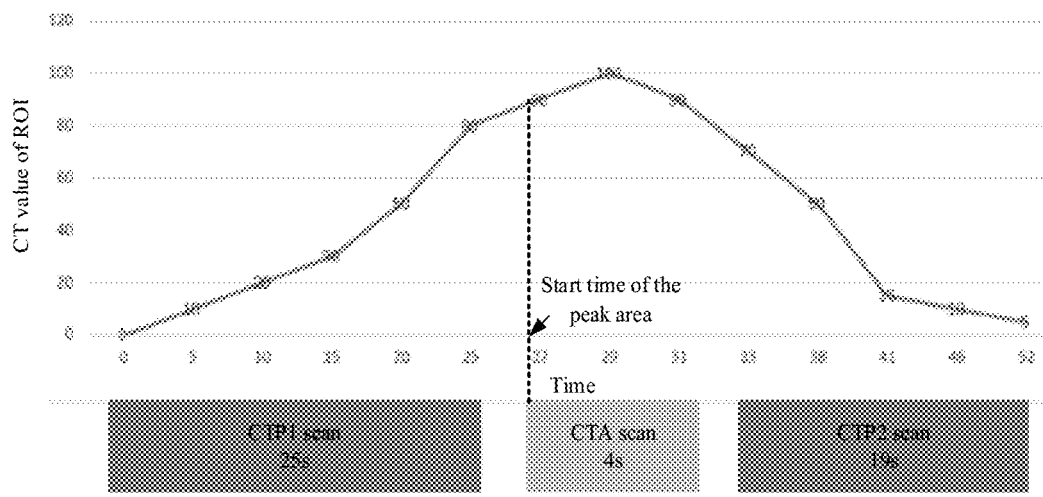
FIG. 3 is a schematic diagram illustrating scan sequence parameters of scan sequences.

Next, as shown in FIG. 2, the operator manually adjusts a scan range of the CTP1 scan sequence by using a positioning box, then manually adjusts a scan range of the CTP2 scan sequence to be consistent with the scan range of the CTP1 scan sequence, and manually adjusts a scan range of the CTA scan sequence to align its head direction with the CTP1 scan sequence and the CTP2 scan sequence. Finally, since default scan start time of the CTA scan sequence may be inaccurate, the scan start time of the CTA scan sequence is manually set to the start time of the aforementioned peak area, as shown in FIG. 3. Parameters of the CTP1 scan sequence and the CTP2 scan sequence are manually adjusted such that a scan duration of the CTP1 scan sequence may cover a period of time before the start of the CTA scan sequence, and a scan duration of the CTP2 scan sequence may cover a period of time after the end of the CTA scan sequence.

Manually setting the parameters of each scan sequence can be less efficient in operation and prone to misoperation. For example, in a combined CTP-CTA scan, the scan range of each scan sequence is manually adjusted by the operator, resulting in low operating efficiency. Moreover, the CTP scan sequence corresponds to the head, while the CTA scan sequence corresponds to the head and neck. Since each scan sequence corresponds to a different scanned position, a manual adjustment cannot generally be completed in one step, and the manual adjustment is performed several times, which causes the operation to be cumbersome.

Figure 4:
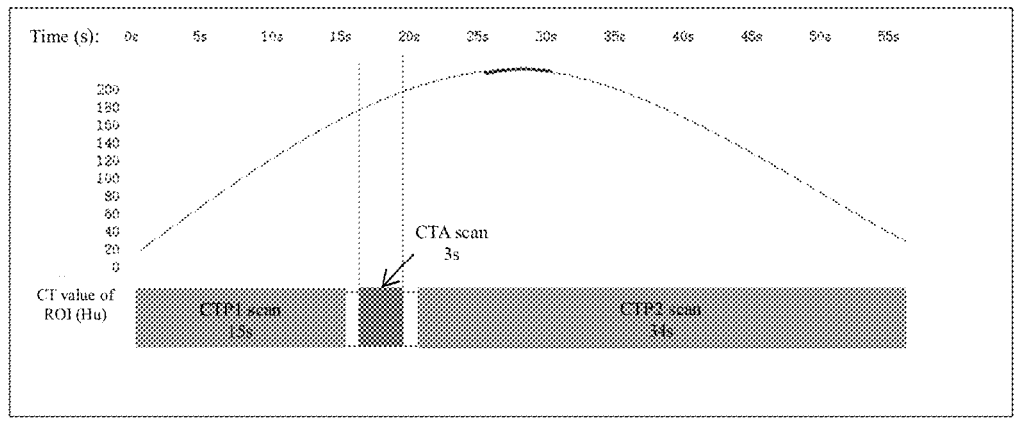
FIG. 4 is another schematic diagram illustrating scan sequence parameters of scan sequences.
Figure 5:
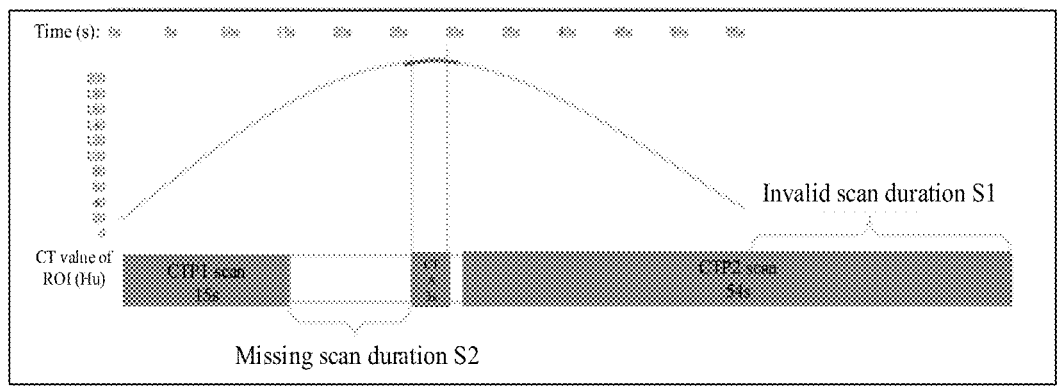
FIG. 5 is a schematic diagram after the scan sequence parameters of the scan sequences shown in FIG. 4 have been manually adjusted.

A scan peak time may be manually recorded at the end of the test scan, and then the scan peak time may be manually set as the scan start time of the CTA scan sequence. Such a manual operation can be prone to misoperation. For example, in a possible case, as shown in FIG. 4, the default scan start time of the CTA scan sequence is earlier than the scan peak time. If the scan start time of the CTA scan sequence is directly adjusted manually to the scan peak time, a problem as shown in FIG. 5 may occur. Referring to FIG. 5, due to a change in the scan start time of the CTA scan sequence, the scan duration of the CTP2 scan sequence may be sequentially shifted backward, resulting in an invalid scan duration S1, and a missing scan duration S2 between the CTP1 scan sequence and the CTA scan sequence. In this case, the operator can manually increase the scan duration of the CTP1 scan sequence and reduce the scan duration of the CTP2 scan sequence, which is cumbersome and inefficient.

Figure 6:
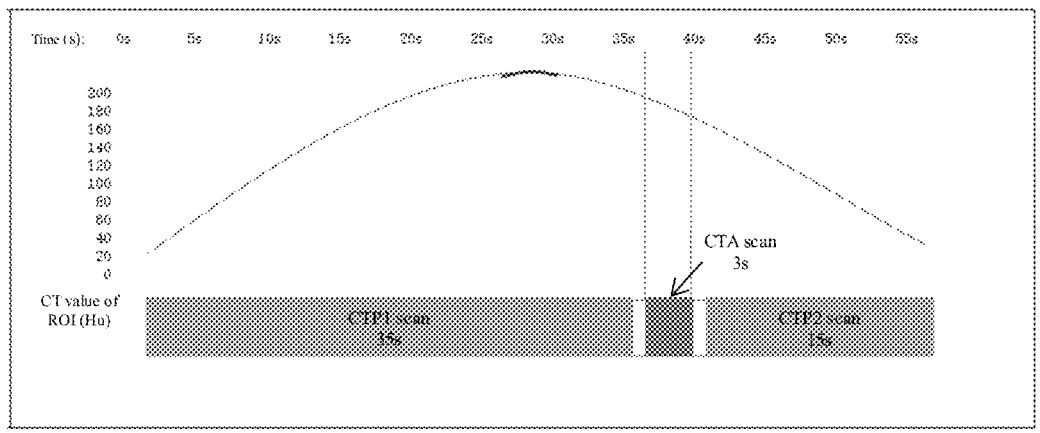
FIG. 6 is another schematic diagram illustrating scan sequence parameters of scan sequences.
Figure 7:
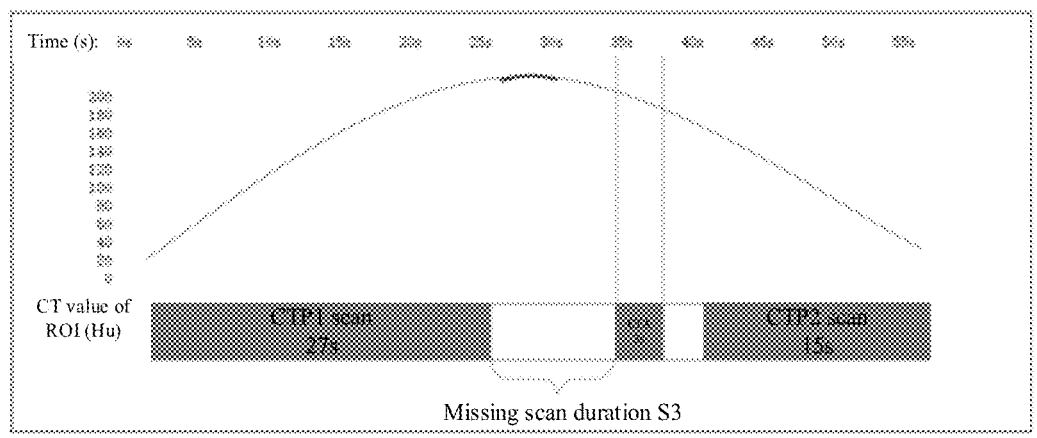
FIG. 7 is a schematic diagram after the scan sequence parameters of the scan sequences shown in FIG. 6 have been manually adjusted.
Figure 8:
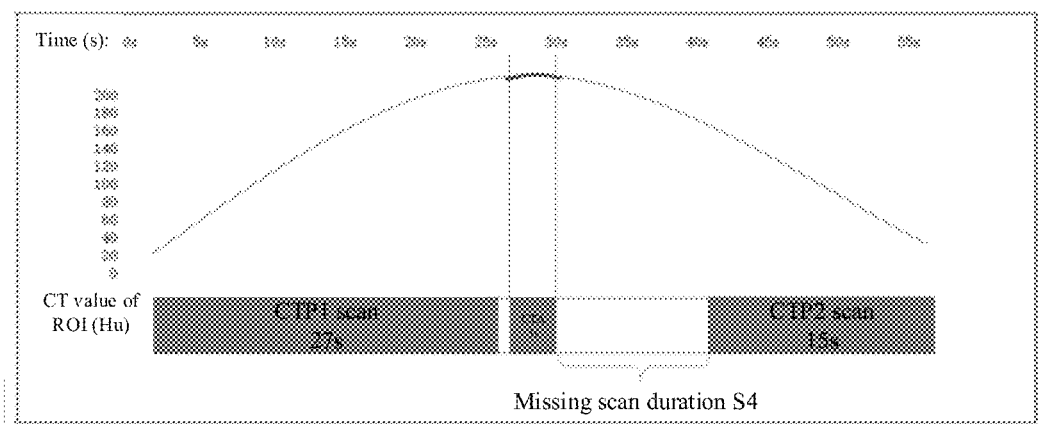
FIG. 8 is a schematic diagram after the scan sequence parameters of the scan sequences shown in FIG. 7 have been manually adjusted.
Figure 9:
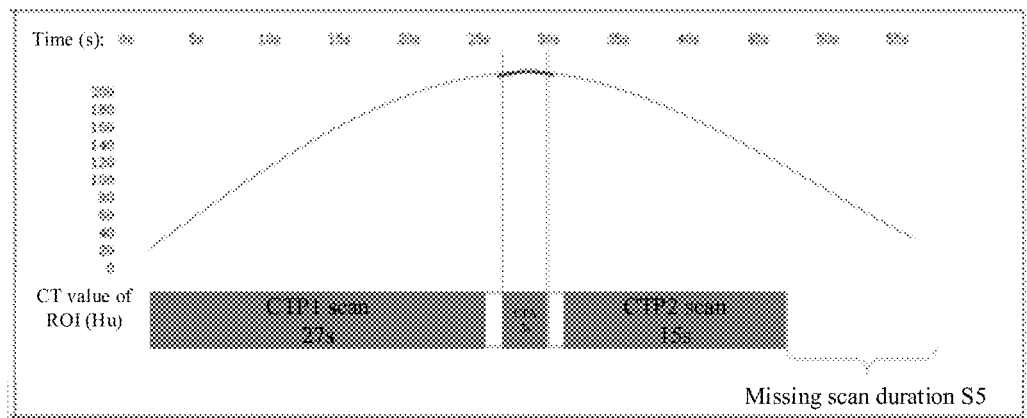
FIG. 9 is a schematic diagram after the scan sequence parameters of the scan sequences shown in FIG. 8 have been manually adjusted in the related art.

For another example, in another possible case, as shown in FIG. 6, the default scan start time of the CTA scan sequence is later than the scan peak time. In this case, the operator can manually adjust the scan duration of the CTP1 scan sequence first. Referring to FIG. 7, due to the adjustment of the scan duration of the CTP1 scan sequence, a missing scan duration S3 occurs between the CTP1 scan sequence and the CTA scan sequence. The next step is to manually adjust the scan start time of the CTA scan sequence. Referring to FIG. 8, due to the adjustment of the scan start time of the CTA scan sequence, a missing scan duration S4 occurs between the CTA scan sequence and the CTP2 scan sequence. The next step is to manually adjust the scan start time of the CTP2 scan sequence. Referring to FIG. 9, due to the adjustment of the scan start time of the CTP2 scan sequence, a missing scan duration S5 occurs after the CTP2 scan sequence. Therefore, the scan duration of the CTP2 scan sequence is further increased to finally meet scanning requirements. It can be seen that the manual setting of the parameters of each scan sequence in the related art involves several manual adjustments, which is cumbersome and inefficient in operation.

Embodiments of the present disclosure provide a multi-sequence scanning method and apparatus, device, and CT system to improve the efficiency of multi-sequence scanning.

Figure 10:
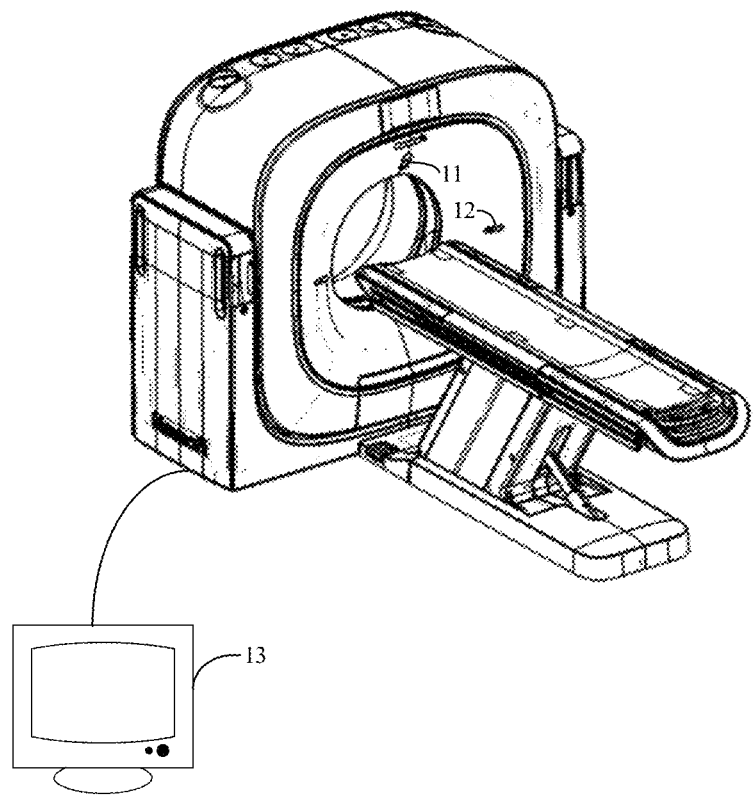
FIG. 10 is a schematic diagram illustrating a CT system for implementing a multi-sequence scanning method.

Firstly, an example scenario for implementing a multi-sequence scanning method is described. FIG. 10 is a schematic diagram of a CT system for implementing a multi-sequence scanning method. Referring to FIG. 10, the CT system may include a ray source 11, a detector 12, an electronic device 13, and other related components illustrated but not labelled in FIG. 10. The ray source 11 may be configured to emit rays. The detector 12 may be configured to detect an attenuated ray signal after the rays pass through a scanned object, convert the attenuated ray signal into an electrical signal, and send the electrical signal to the electronic device 13. The electronic device 13 may be configured to perform the multi-sequence scanning method according to the embodiments of the present disclosure. Before the ray source 11 and the detector 12 operate, the electronic device 13 may configure scan sequence parameters for a plurality of scan sequences in a scan protocol to obtain a target scan protocol, and in response to receiving a scan command, control the CT system to scan the scanned object according to the scan sequence parameters configured in the target scan protocol, thereby realizing automatic configuration for the scan sequence parameters, reducing the risk of misoperation during the multi-sequence scanning, and improving the efficiency of the multi-sequence scanning.

Figure 11:
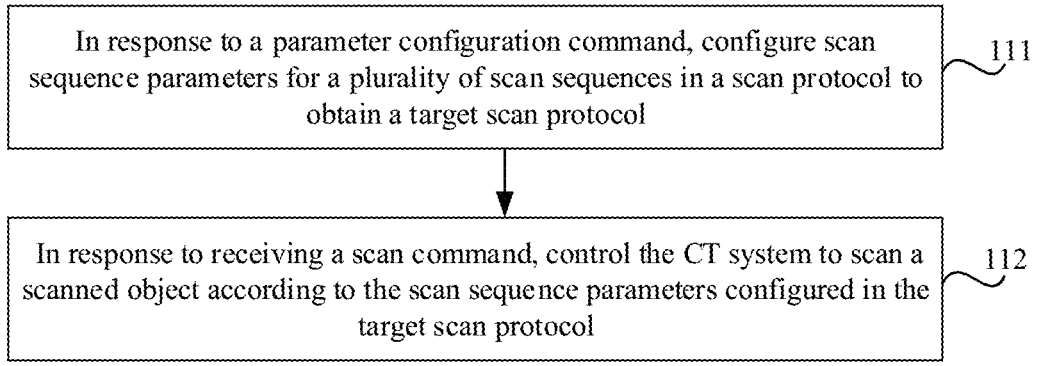
FIG. 11 is a flowchart illustrating a multi-sequence scanning method.

FIG. 11 is a flowchart illustrating a multi-sequence scanning method. Referring to FIG. 11, the multi-sequence scanning method may include elements 111 and 112.

At 111, in response to a parameter configuration command, scan sequence parameters are configured for a plurality of scan sequences in a scan protocol to obtain a target scan protocol. The scan sequence parameters include a scan start time and a scan duration of each of the scan sequences, and a scan switching duration between the scan sequences. A total scan duration of the scan sequences in the target scan protocol is configured to be less than or equal to a preset total scan duration. The scan switching duration between the scan sequences is configured in a shortest duration mode, which indicates that time between the end of one scan sequence and the start of the next scan sequence is the shortest and may be used as an option for the scan switching duration.

At 112, in response to receiving a scan command, the CT system is controlled to scan a scanned object according to the scan sequence parameters configured in the target scan protocol.

As above, scan sequence parameters may be automatically configured for a plurality of scan sequences in a scan protocol in response to a parameter configuration command to obtain a target scan protocol, and then in response to receiving a scan command, a CT system may be controlled to scan a scanned object according to the scan sequence parameters configured in the target scan protocol. There is no need to manually set the parameters for each scan sequence. Instead, parameter setting of multi-sequence scanning is automated, reducing the risk of misoperation during the multi-sequence scanning, and improving the efficiency of the multi-sequence scanning.

A scan sequence may correspond to a scanned position of a scanned object. For example, a CTA scan sequence is used to scan the head and neck of the scanned object to check arteries of the head and neck of the scanned object, and a CTP scan sequence is used to scan the head of the scanned object to check blood perfusion of brain tissues of the scanned object. In practice, a plurality of scanned positions are usually set for the scanned object to better determine the physical condition of the scanned object, thus a multi-sequence scanning method may be adopted. For example, in the stroke examination described above, a combined CTP-CTA scan is usually performed on the head and neck.

A user may set the number of scan sequences and the scan position corresponding to each of the scan sequences according to actual examination requirements, which is not limited in the embodiments of the present disclosure.

In practice, after a plurality of scan sequences are set for the scanned object, scan sequence parameters of each of the scan sequences and CT system operating parameters corresponding to each scan sequence may be set. The scan sequence parameters may be configured to characterize time parameters related to the scan sequences, which, for example, may include a scan start time, a scan duration, a scan switching duration between the scan sequences, etc. The CT system operating parameters may be configured to characterize hardware parameters of the CT system operation, which, for example, may include a scan length, rotation speed, and slice size of the CT system, etc.

Scan sequence parameters may be configured for a plurality of scan sequences in a scan protocol in response to a parameter configuration command, at 111. The parameter configuration command is configured to trigger a configuration process for the scan protocol. The parameter configuration command may be generated in response to a user operation, or may be generated automatically when the scanned object is detected, which is not limited in the embodiments of the present disclosure. For example, a parameter configuration button may be set, and when the user presses the parameter configuration button, the parameter configuration command may be generated, thereby performing element 111.

As an example, the scan protocol may include a plurality of scan sequence parameters to be configured. In the combined CTP-CTA scan performed on the head and neck, where the scan sequences may include the CTP1 scan sequence, the CTA scan sequence, and the CTP2 scan sequence in that order, the scan protocol may include the following contents.

A. Positioning Film Sequence

During the scanning process, a position, angle, and layer thickness to be scanned may be marked on a positioning film, and the CT system may then perform scans according to the marks on the positioning film. The positioning film sequence may be determined in a similar way to the related art, which will not be repeated here.

B. Peak Test Sequence

The following variables may be defined for the peak test sequence:

1. ROI peak time (MHT, MaxHUTime), which is used to record the scan peak time as described above.
2. ROI threshold (ROI_Threshold), which is used to determine whether the scan peak time is reached.

C. CTP1 Scan Sequence

A variable of scan start time (CTP1ScanDelayTime) may be defined for the CTP1 scan sequence, and a default thereof may be, for example, 5 seconds. The scan start time may characterize time between when the user issues a scan command and when the CT system actually starts to scan. For example, the scan start time defaults to 5 seconds, which indicates that a scan with the CTP1 scan sequence will start 5 seconds after the user issues the scan command.

D. CTA Scan Sequence

The following variables may be defined for the CTA scan sequence:

1. Advance scan time (AST), a default of which may be, for example, 2 seconds. For the CTA scan sequence, the scan start time is generally a few seconds earlier than the scan peak time, such that the CTA scan sequence may cover the scan peak time, so as to avoid the problem that the scan duration of the CTA scan sequence cannot cover the scan peak time due to mechanical measurement errors, and to better achieve the purpose of CTA scanning.
2. Scan start time (CTAScanDelayTime), which is null by default.

E. CTP2 Scan Sequence

A variable of scan start time (CTP2ScanDelayTime) may be defined for the CTP2 scan sequence, and a default thereof may be null.

F. Total Scan Duration (TMax)

The total scan duration is configured to characterize time from the start of the CTP1 scan sequence to the end of the CTP2 scan sequence, and a default thereof may be, for example, 50 seconds.

An initial value (default value) of each parameter in the above scan protocol may be set according to actual conditions, which is not limited in the embodiments of the present disclosure. The foregoing is merely an example description of the scan protocol, and is not intended to limit the present disclosure. The user may set different scan protocols according to actual conditions, which is not limited in the embodiments of the present disclosure.

Figure 12:
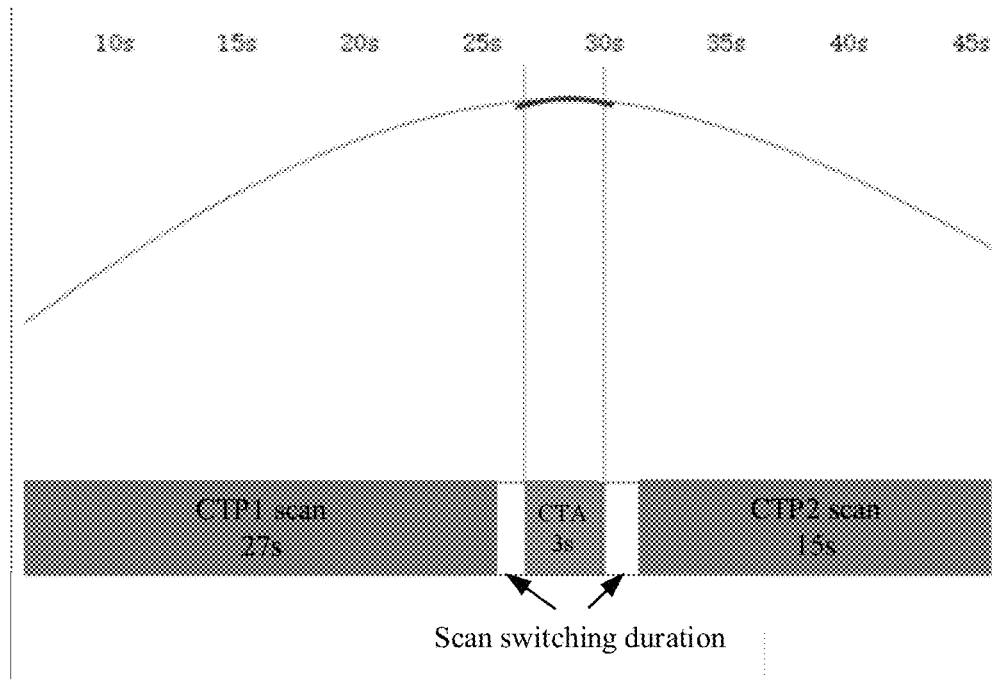
FIG. 12 is a schematic diagram illustrating a scan switching duration in a multi-sequence scanning method.

Regarding the scan sequence parameters, as described above, the scan sequence parameters may be configured to characterize the time parameters related to the scan sequences, which, for example, may include the scan start time, the scan duration, the scan switching duration between the scan sequences, etc. The scan start time is configured to characterize the time when a scan performed with the scan sequences starts, and the scan duration is configured to characterize time from the start of the scan sequences to the end of the scan sequences. As for the scan switching duration, as shown in FIG. 12, it may be configured to characterize time from the end of a current scan sequence to the start of the next scan sequence.

After configuring the scan sequence parameters for the scan protocol, e.g., after setting a value of each scan sequence parameter in the scan protocol, a target scan protocol may be obtained. A total scan duration of the scan sequences in the target scan protocol is configured to be less than or equal to a preset total scan duration, and the scan switching duration between the scan sequences is configured in a shortest duration mode. In this way, actual scanning requirements can be better met, an invalid scanning caused by a longer total scan duration can be avoided, and scan results being affected by an excessive time resolution due to a longer scan switching duration between the scan sequences can be avoided.

The process of configuring the scan sequence parameters for the scan protocol will be further described below.

In an example embodiment, the scan sequences may include the CTA scan sequence. Considering that the CTA scan sequence covers the scan peak time, the scan peak time may be monitored initially, and then the scan start time of the CTA scan sequence may be configured according to the monitored scan peak time, such that the scan start time of the scan sequence is earlier than or concurrent with the scan peak time. The scan peak time is the time when an average of CT values of a region of interest reaches a preset threshold, and the region of interest is a preset region where the CT values are to be monitored.

In an example, the head and neck of the scanned object are scanned with the CTA scan sequence, and the region of interest may be an area corresponding to a certain portion of the head or neck of the scanned object. In practice, the region of interest may be customized according to a size, shape, and number of a lesion. For example, the shape of the region of interest may generally include a circle, an ellipse, a rectangle, and a polygon, and the number of the region of interest may vary from one to several. By monitoring the CT values of the region of interest, the scan peak time may be determined, and thus the scan start time of the CTA scan sequence may be determined.

For example, an initial scan protocol is the scan protocol described above. After a test scan has started, the CT values of the region of interest may be monitored in real time. When the average of the CT values of the region of interest reaches the ROI threshold (ROI_Threshold), the time for the average of the CT values to reach the ROI threshold may be recorded in the variable of MHT, and the test scan ends. In this case, the time recorded in the variable of MHT may be determined as the scan start time of the CTA scan sequence, e.g., the scan start time of the CTA scan sequence is the scan peak time. Alternatively, in order to avoid the problem that the scan duration of the CTA scan sequence cannot cover the scan peak time due to mechanical measurement errors, the advance scan time (AST) may be subtracted from the time recorded in the variable of MHT. For example, if the scan peak time is the 17th second, meaning that the time recorded in the variable of MHT is 17 seconds, and the advance scan time is 2 seconds, then it may be determined that the scan start time of the CTA scan sequence is the 15th second. In this case, the scan start time of the CTA scan sequence is earlier than the scan peak time.

As above, the scan peak time may be monitored initially, and then the scan start time of the scan sequence covering the scan peak time may be determined according to the scan peak time, such that the scan start time of the scan sequence is earlier than or concurrent with the scan peak time, and thus the scan sequence covers the scan peak time. This process may be automatically monitored and completed by the system without manual recording or manual setting by the user, which reduces the risk of misoperation and improves the operating efficiency.

In an example embodiment, the scan sequences may include a first scan sequence and a second scan sequence, and the first scan sequence is a previous scan sequence of the second scan sequence. Configuring the scan sequence parameters for the plurality of scan sequences in the scan protocol may include: monitoring the scan peak time initially, where the scan peak time is the time when an average of CT values of a region of interest reaches a preset threshold, and the region of interest is a preset region where the CT values are to be monitored; then configuring the scan start time of the second scan sequence according to the monitored scan peak time, such that the scan start time of the second scan sequence is earlier than or concurrent with the scan peak time; and finally, adjusting the scan sequence parameters of the first scan sequence such that time between the scan start time of the first scan sequence and the scan start time of the second scan sequence is equal to a sum of the scan duration of the first scan sequence and the scan switching duration, where the scan switching duration is the time to switch from the first scan sequence to the second scan sequence.

In an example, the first scan sequence may be the CTP scan sequence, and the second scan sequence may be the CTA scan sequence. Then, according to the above method, the scan start time of the CTA scan sequence may be initially determined according to the scan peak time, and then the scan sequence parameters of the CTP scan sequence may be adjusted according to the scan start time of the CTA scan sequence, such that the time between the scan start time of the CTP scan sequence and the scan start time of the CTA scan sequence is equal to the sum of the scan duration of the CTP scan sequence and the scan switching duration.

In an example embodiment, adjusting the scan sequence parameters of the first scan sequence may include: adjusting the scan duration of the first scan sequence by adjusting the number of scan circles for the first scan sequence, a scan duration per scan circle for the first scan sequence, or both. When the first scan sequence is the first one of the scan sequences, adjusting the scan sequence parameters of the first scan sequence may include at least one of: adjusting the scan start time of the first scan sequence; or adjusting the scan duration of the first scan sequence by adjusting the number of scan circles for the first scan sequence, a scan duration per scan circle for the first scan sequence, or both.

The scan duration of the scan sequence may be a product of the number of scan circles and the scan duration per scan circle of the CT system corresponding to the scan sequence. Therefore, the scan duration of the first scan sequence may be adjusted by adjusting the number of scan circles for the first scan sequence, the scan duration per scan circle for the first scan sequence, or both.

In some examples, the scan start time of the first scan sequence may be adjusted when the first scan sequence is the first one of the scan sequences, since there are no other scan sequences before the first scan sequence, and adjusting the scan start time of the first scan sequence may not directly affect the scan sequence parameters of other scan sequences. For instance, when the first scan sequence is the first one of the scan sequences, at least one of the scan start time of the first scan sequence, the number of scan circles or the scan duration per scan circle for the first scan sequence may be adjusted. For example, the scan duration of the first scan sequence may be adjusted by adjusting the number of scan circles for the first scan sequence, the scan duration per scan circle for the first scan sequence, or both, and then it may be determined whether the time between the scan start time of the first scan sequence and the scan start time of the second scan sequence is equal to the sum of the scan duration of the first scan sequence and the scan switching duration. If not, the scan start time of the first scan sequence may be further adjusted.

In this way, after the scan start time of the second scan sequence is determined, the scan sequence parameters of the previous scan sequence (that is, the first scan sequence) of the second scan sequence may be automatically adjusted according to the scan start time to meet the scanning requirements, which can reduce the risk of misoperation and improve the operating efficiency compared with the manual setting method.

In an example embodiment, the first scan sequence may have initial/default scan sequence parameters. If the default scan sequence parameters of the first scan sequence satisfies the condition that time between an initial scan start time of the first scan sequence and the scan start time of the second scan sequence is equal to a sum of an initial scan duration of the first scan sequence and the scan switching duration, after the scan start time of the second scan sequence is determined, there is no need to adjust the scan sequence parameters of the first scan sequence. Therefore, it is possible to perform a judgment process before adjusting the scan sequence parameters of the first scan sequence.

For example, an actual scan end time of the first scan sequence may be determined according to initial scan start time, an initial number of scan circles, and an initial scan duration per scan circle for the first scan sequence. Then, a theoretical scan end time of the first scan sequence may be obtained by subtracting the scan switching duration between the second scan sequence and the first scan sequence from the scan start time of the second scan sequence. In response to the actual scan end time being inconsistent with the theoretical scan end time, the scan sequence parameters of the first scan sequence may be adjusted.

For example, an initial scan duration of the scan sequence may be determined according to a product of the initial number of scan circles and the initial scan duration per scan circle for the scan sequence. When the first scan sequence is the first one of the scan sequences, the initial scan start time of the first scan sequence may be 0, thus the initial scan duration of the first scan sequence is the actual scan end time of the first scan sequence.

The scan start time of the second scan sequence may be obtained according to the scan peak time in the above-mentioned manner. As for the scan switching duration, after determining the system operating parameters corresponding to the first scan sequence and the second scan sequence, the scan switching duration between the first scan sequence and the second scan sequence may be determined. As explained above, the CT system operating parameters may be configured to characterize the hardware parameters of the CT system operation, which, for example, may include the rotation speed and slice size of the CT system, etc. For example, at the end of the first scan sequence, the system operating parameters of the CT system are a bed size of 200 mm, the rotation speed of 0.4 seconds/circle, and the slice size of 128*0.625 mm; while at the start of the second scan sequence, the system operating parameters of the CT system are the bed size of 100 mm, the rotation speed of 0.2 seconds/circle, and the slice size of 512*0.625 mm. In this case, the scan switching duration may include time to move the bed, rotation speed adjustment time, and slice size adjustment time. Therefore, after determining the system operating parameters corresponding to the first scan sequence and the second scan sequence, the scan switching duration between the first scan sequence and the second scan sequence may be determined.

As above, the actual scan end time of the first scan sequence may be obtained, and the theoretical scan end time of the first scan sequence may be obtained by subtracting the scan switching duration between the second scan sequence and the first scan sequence from the scan start time of the second scan sequence. Then, it may be determined whether the actual scan end time of the first scan sequence is consistent with the theoretical scan end time of the first scan sequence. If the actual scan end time of the first scan sequence is not consistent with the theoretical scan end time of the first scan sequence, the scan sequence parameters of the first scan sequence may be adjusted such that time between the scan start time of the first scan sequence and the scan start time of the second scan sequence is equal to a sum of the scan duration of the first scan sequence and the scan switching duration. If the actual scan end time of the first scan sequence is consistent with the theoretical scan end time of the first scan sequence, there is no need to perform the step of adjusting the scan sequence parameters of the first scan sequence, which can further improve the operating efficiency.

In an example embodiment, the scan sequences may further include a third scan sequence, where the third scan sequence is the next scan sequence of the second scan sequence, and the third scan sequence is the last one of the scan sequences. Configuring the scan sequence parameters for the plurality of scan sequences in the scan protocol may further include: adjusting scan sequence parameters of the third scan sequence such that the time between a scan end time of the third scan sequence and the scan start time of the first scan sequence is less than or equal to the preset total scan duration. The preset total scan duration may be set according to actual conditions, which is not limited in the embodiments of the present disclosure.

For instance, when the scan sequences include three scan sequences in the order of the first scan sequence, the second scan sequence, and the third scan sequence, the scan sequence parameters (such as the scan start time and the scan duration) of the first scan sequence may be determined according to the scan start time of the second scan sequence, and then the scan sequence parameters of the third scan sequence may be adjusted such that the time between the scan end time of the third scan sequence and the scan start time of the first scan sequence is less than or equal to the preset total scan duration. The scan end time of the third scan sequence may be a sum of the scan start time of the third scan sequence and the scan duration of the third scan sequence.

Therefore, before adjusting the scan sequence parameters of the third scan sequence, the scan start time of the third scan sequence may be determined according to the scan sequence parameters of the second scan sequence. For example, a sum of the following three time may be determined as the scan start time of the third scan sequence: the scan start time of the second scan sequence, the scan duration of the second scan sequence, and the scan switching duration between the second scan sequence and the third scan sequence.

For example, in the combined CTP-CTA scan performed on the head and neck, the first scan sequence is the CTP1 scan sequence, the second scan sequence is the CTA scan sequence, and the third scan sequence is the CTP2 scan sequence, and a scanning order is the CTP1 scan sequence, the CTA scan sequence, and the CTP2 scan sequence. In this case, after determining the scan sequence parameters of the CTP1 scan sequence according to the scan start time of the CTA scan sequence, the scan start time of the CTP2 scan sequence may be determined initially according to the scan sequence parameters of the CTA scan sequence. Then, the scan sequence parameters of the CTP2 scan sequence may be adjusted such that the time between the scan end time of the CTP2 scan sequence and the scan start time of the CTP1 scan sequence is less than or equal to the preset total scan duration. Adjusting the scan sequence parameters of the CTP2 scan sequence may include adjusting the scan duration of the CTP2 scan sequence by adjusting the number of scan circles for the CTP2 scan sequence, the scan duration per scan circle for the CTP2 scan sequence, or both.

In this way, the scan sequence parameters of the third scan sequence may be automatically configured after the scan sequence parameters of the first scan sequence and the second scan sequence are determined, eliminating manually setting of the scan sequence parameters of each scan sequence, which can reduce the risk of misoperation and improve the operating efficiency.

As above, the system operating parameters of the CT system may affect the scan sequence parameters of the scan sequences. For example, the scan duration of the scan sequence may be adjusted by adjusting the number of scan circles, the scan duration per scan circle for the scan sequence, or both. Moreover, in practice, the system operating parameters of the CT system may be default values, or may be values input by the user according to actual scanning conditions. If the system operating parameters are input by the user, the system operating parameters can be adjusted according to the user input before configuring the scan sequence parameters of the scan sequences. For instance, the hardware parameters (that is, the system operating parameters described above) of the CT system may be determined before software parameters (e.g., the scan sequence parameters described above) of the CT system are configured.

In an example embodiment, the parameter configuration command may include one or more system operating parameters to be adjusted and values of the system operating parameters. Before configuring the scan sequence parameters for the plurality of scan sequences in the scan protocol, the method may further include: determining one or more target system operating parameters to be adjusted in synchronization with each of the system operating parameters to be adjusted, according to a parameter adjustment correlation and each of the system operating parameters to be adjusted, where the parameter adjustment correlation is configured to characterize a synchronous adjustment relationship between each of the system operating parameters to be adjusted and respective target system operating parameters; and then adjusting values of the respective target system operating parameters according to the value of each of the system operating parameters to be adjusted.

For example, the parameter adjustment correlation may be preset according to the scan sequences with the synchronous adjustment relationship, and the parameter adjustment correlation may be manifested as a parameter adjustment table, a parameter adjustment file, and the like. However, specific forms and contents of the parameter adjustment correlation are not limited in the embodiments of the present disclosure. For example, in the combined CTP-CTA scan performed on the head and neck, the scan sequences are the CTP1 scan sequence, the CTA scan sequence, and the CTP2 scan sequence in that order, and the parameter adjustment correlation may be shown in Table 1.

TABLE 1

|  | CTP1 | CTA | CTP2 |
| --- | --- | --- | --- |
| Scan start position | AA | AA | AA |
| Scan length | AA | N/A | AA |
| Rotation speed | AA | AA | AA |
| Slice | AA | AA | AA |
| Current | AA | N/A | AA |

Referring to Table 1, for any system operating parameter, "AA" corresponding to a scan sequence indicates that the system operating parameter of the scan sequence changes synchronously when the system operating parameters for other scan sequences change. For any system operating parameter, "N/A" corresponding to a scan sequence indicates that the system operating parameter of the scan sequence does not change synchronously when the system operating parameters for other scan sequences change.

For example, the user changes the rotation speed corresponding to the CTP1 scan sequence from 0.3 to 1.0, that is, the parameter configuration command includes the rotation speed as the system operating parameter to be adjusted, and the value of the system operating parameter is 1.0. In this case, the target system operating parameters to be adjusted in synchronization with the rotation speed for the CTP1 scan sequence may be determined according to the parameter adjustment correlation as shown in Table 1, and include the rotation speed for the CTA scan sequence and the rotation speed for the CTP2 scan sequence. Therefore, the rotation speed for the CTA scan sequence and the rotation speed for the CTP2 scan sequence may be synchronized to 1.0 based on the rotation speed for the CTP1 scan sequence. The scan sequence parameters may be automatically configured for the scan protocol after the system operating parameters have been adjusted.

As another example, the user modifies the scan length corresponding to the CTP1 scan sequence to 120, that is, the parameter configuration command includes the scan length as the system operating parameter to be adjusted, and the value of the system operating parameter is 120. In this case, the target system operating parameter to be adjusted in synchronization with the scan length for the CTP1 scan sequence may be determined according to the parameter adjustment correlation as shown in Table 1, and include the scan length for the CTP2 scan sequence. Therefore, the scan length for the CTP2 scan sequence may be synchronized to 120 based on the scan length for the CTP1 scan sequence. The scan sequence parameters may be automatically configured for the scan protocol after the system operating parameters have been adjusted.

It should be understood that the way in which the user modifies the system operating parameters is not limited in the embodiments of the present disclosure. For example, the user may modify the system operating parameters by dragging the positioning box for the scan sequence, or may modify the system operating parameters by manually inputting the system operating parameters, etc. In particular, for the modification of the system operating parameters by dragging the positioning box, the parameter configuration command may be generated by the system monitoring a change in the system operating parameters, while for the modification of the system operating parameters by manually inputting the system operating parameters, the parameter configuration command may be generated in response to the user's input operation.

In this way, after the user modifies a system operating parameter for a certain scan sequence, system operating parameters for other scan sequences that have a synchronous adjustment relationship with the system operating parameter for the scan sequence may be automatically adjusted, without manually adjusting the system operating parameters for other scan sequences by the user, which can reduce the risk of misoperation and improve the operating efficiency.

Figure 13:
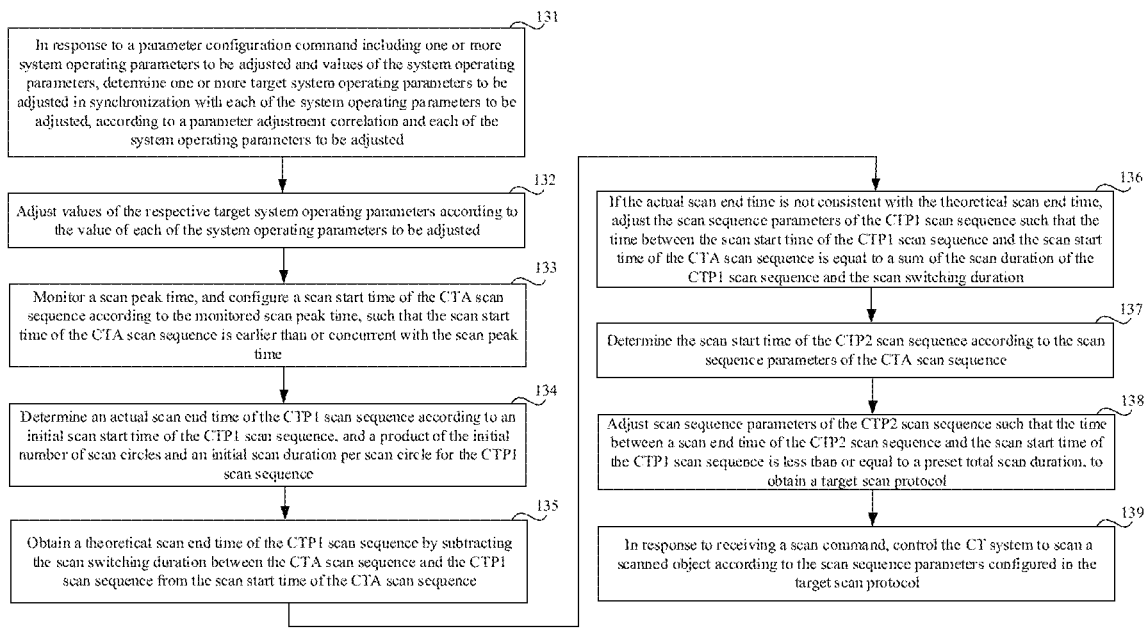
FIG. 13 is a flowchart illustrating a multi-sequence scanning method.

The multi-sequence scanning method according to the present disclosure will be described below by taking the combined CTP-CTA scan performed on the head and neck as an example. Referring to FIG. 13, the scan sequences may include the CTP1 scan sequence, the CTA scan sequence, and the CTP2 scan sequence in that order, and the multi-sequence scanning method may include elements 131-139.

At 131, in response to a parameter configuration command including one or more system operating parameters to be adjusted and values of the system operating parameters, one or more target system operating parameters to be adjusted in synchronization with each of the system operating parameters to be adjusted are determined, according to a parameter adjustment correlation and each of the system operating parameters to be adjusted, where the parameter adjustment correlation is configured to characterize a synchronous adjustment relationship between each of the system operating parameters to be adjusted and respective target system operating parameters.

At 132, values of the respective target system operating parameters are adjusted according to the value of each of the system operating parameters to be adjusted.

At 133, a scan peak time is monitored, and a scan start time of the CTA scan sequence is configured according to the monitored scan peak time, such that the scan start time of the CTA scan sequence is earlier than or concurrent with the scan peak time.

At 134, an actual scan end time of the CTP1 scan sequence is determined according to an initial scan start time of the CTP1 scan sequence, and a product of the initial number of scan circles and an initial scan duration per scan circle for the CTP1 scan sequence.

At 135, a theoretical scan end time of the CTP1 scan sequence is obtained by subtracting the scan switching duration between the CTA scan sequence and the CTP1 scan sequence from the scan start time of the CTA scan sequence.

At 136, if the actual scan end time is not consistent with the theoretical scan end time, the scan sequence parameters of the CTP1 scan sequence are adjusted such that the time between the scan start time of the CTP1 scan sequence and the scan start time of the CTA scan sequence is equal to a sum of the scan duration of the CTP1 scan sequence and the scan switching duration. The scan switching duration is the time to switch from the CTP1 scan sequence to the CTA scan sequence. If the actual scan end time is consistent with the theoretical scan end time, element 137 may be performed directly.

At 137, the scan start time of the CTP2 scan sequence is determined according to the scan sequence parameters of the CTA scan sequence.

At 138, scan sequence parameters of the CTP2 scan sequence are adjusted such that the time between a scan end time of the CTP2 scan sequence and the scan start time of the CTP1 scan sequence is less than or equal to a preset total scan duration, to obtain a target scan protocol.

At 139, in response to receiving a scan command, the CT system is controlled to scan a scanned object according to the scan sequence parameters configured in the target scan protocol.

Specific embodiments of the foregoing steps have been described in detail above, and will not be repeated here. It should also be understood that the method embodiments described above are presented as a series of combinations of actions for simplicity of description. However, those skilled in the art should understand that the present disclosure is not limited by the sequence of actions described above. Moreover, those skilled in the art should also be aware that the embodiments described above are exemplary embodiments, and the steps involved are not necessarily essential for the present disclosure.

With the above-described methods, after the user modifies a system operating parameter for a certain scan sequence, system operating parameters for other scan sequences that have a synchronous adjustment relationship with the system operating parameter for the scan sequence may be automatically adjusted, without manually adjusting the system operating parameters for other scan sequences by the user, which can reduce the risk of misoperation and improve the operating efficiency. After the system operating parameters are adjusted synchronously, the scan sequence parameters of each scan sequence may be automatically configured for the scan protocol without manually setting the parameters for each scan sequence, which can automate parameter setting of multi-sequence scanning, further reduce the risk of misoperation during the multi-sequence scanning, and improve the efficiency of the multi-sequence scanning.

Figure 14:
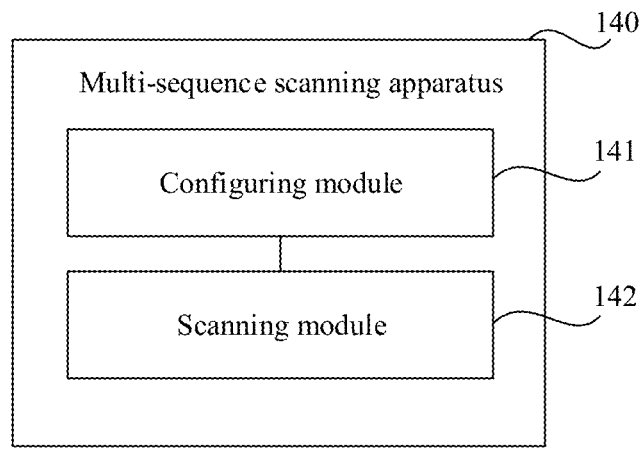
FIG. 14 is a block diagram illustrating a multi-sequence scanning apparatus.

Embodiments of the present disclosure provide a multi-sequence scanning apparatus, which may become part or all of a medical device such as a CT system through software, hardware, or a combination of both. Referring to FIG. 14, a multi-sequence scanning apparatus 140 may include a configuring module 141 and a scanning module 142.

The configuring module 141 is configured to: in response to a parameter configuration command, configure scan sequence parameters for a plurality of scan sequences in a scan protocol to obtain a target scan protocol, where the scan sequence parameters include a scan start time and a scan duration of each of the scan sequences, and a scan switching duration between the scan sequences, a total scan duration of the scan sequences in the target scan protocol is configured to be less than or equal to a preset total scan duration, and the scan switching duration between the scan sequences is configured in a shortest duration mode.

The scanning module 142 is configured to: in response to receiving a scan command, control the CT system to scan a scanned object according to the scan sequence parameters configured in the target scan protocol.

In some examples, the configuring module 141 is configured to: monitor a scan peak time, where the scan peak time is the time when an average of CT values of a region of interest reaches a preset threshold, and the region of interest is a preset region where the CT values are to be monitored; and configure the scan start time of the scan sequence covering the scan peak time according to the monitored scan peak time, such that the scan start time of the scan sequence is earlier than or concurrent with the scan peak time.

In some examples, the scan sequences include a first scan sequence and a second scan sequence, and the first scan sequence is a previous scan sequence of the second scan sequence, and the configuring module 141 is configured to: monitor a scan peak time, where the scan peak time is the time when an average of CT values of a region of interest reaches a preset threshold, and the region of interest is a preset region where the CT values are to be monitored; configure the scan start time of the second scan sequence according to the monitored scan peak time, such that the scan start time of the second scan sequence is earlier than or concurrent with the scan peak time; and adjust the scan sequence parameters of the first scan sequence such that the time between the scan start time of the first scan sequence and the scan start time of the second scan sequence is equal to a sum of the scan duration of the first scan sequence and the scan switching duration, where the scan switching duration is the time to switch from the first scan sequence to the second scan sequence.

In some examples, the configuring module 141 is configured to: adjust the scan duration of the first scan sequence by adjusting the number of scan circles for the first scan sequence, a scan duration per scan circle for the first scan sequence, or both; or when the first scan sequence is the first one of the scan sequences, adjust at least one of the scan start time, the number of scan circles or a scan duration per scan circle for the first scan sequence.

In some examples, the configuring module 141 is configured to: determine an actual scan end time of the first scan sequence according to an initial scan start time, an initial number of scan circles, and an initial scan duration per scan circle for the first scan sequence; obtain a theoretical scan end time of the first scan sequence by subtracting the scan switching duration between the second scan sequence and the first scan sequence from the scan start time of the second scan sequence; and in response to the actual scan end time being inconsistent with the theoretical scan end time, adjust the scan sequence parameters of the first scan sequence.

In some examples, the scan sequences further include a third scan sequence, the third scan sequence is the next scan sequence of the second scan sequence, and the third scan sequence is the last one of the scan sequences, and the configuring module 141 is configured to: adjust scan sequence parameters of the third scan sequence such that the time between a scan end time of the third scan sequence and the scan start time of the first scan sequence is less than or equal to the preset total scan duration.

In some examples, the parameter configuration command includes one or more system operating parameters to be adjusted and values of the system operating parameters, and the multi-sequence scanning apparatus 140 may further include a synchronous adjustment module 143.

The synchronous adjustment module 143 is configured to: before the scan sequence parameters are configured for the plurality of scan sequences in the scan protocol, determine one or more target system operating parameters to be adjusted in synchronization with each of the system operating parameters to be adjusted, according to a parameter adjustment correlation and each of the system operating parameters to be adjusted, where the parameter adjustment correlation is configured to characterize a synchronous adjustment relationship between each of the system operating parameters to be adjusted and respective target system operating parameters; and adjust values of the respective target system operating parameters according to the value of each of the system operating parameters to be adjusted.

Specific manners in which each module in the apparatus according to the above embodiments performs its operation have been described in detail in the corresponding method embodiments, and will not be described in detail here.

Embodiments of the present disclosure provide an electronic device, including: at least one processor; and one or more memories coupled to the at least one processor and storing programming instructions for execution by the at least one processor to perform the above multi-sequence scanning method.

Figure 15:
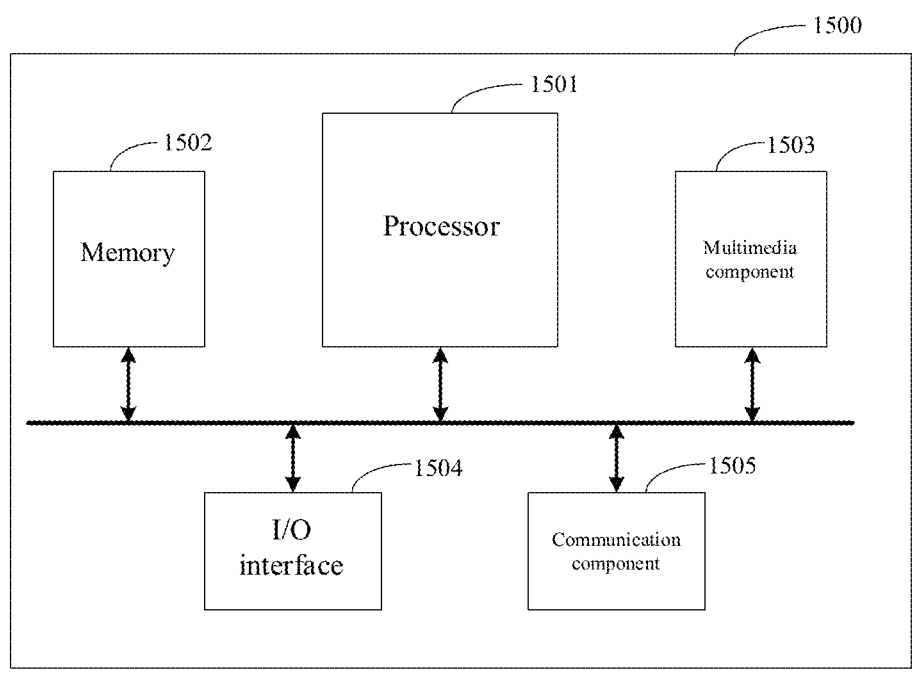
FIG. 15 is a block diagram illustrating an electronic device.

In an example embodiment, the electronic device may be the electronic device 13 included in the CT system as shown in FIG. 10. A block diagram of the electronic device is shown in FIG. 15. Referring to FIG. 15, the electronic device 1500 may include a processor 1501 and a memory 1502. The electronic device 1500 may further include one or more of a multimedia component 1503, an input/output (I/O) interface 1504, and a communication component 1505.

The processor 1501 is configured to control an overall operation of the electronic device 1500 to accomplish all or part of the steps in the above multi-sequence scanning method. The memory 1502 is configured to store various types of data to support operations at the electronic device 1500. These data may include, for example, instructions for any application or method to operate on the electronic device 1500, as well as application-related data, such as the target scan protocol.

The memory 1502 may be implemented by any type of volatile or non-volatile storage device or a combination thereof, such as Static Random Access Memory (SRAM), Electrically Erasable Programmable Read-Only Memory (EEPROM), Erasable Programmable Read-Only Memory (EPROM), Programmable Read-Only Memory (PROM), Read-Only Memory (ROM), magnetic memory, flash memory, magnetic disk or optical disk.

The multimedia component 1503 may include a screen and an audio component. The screen may be a touch screen, for example, and the audio component is configured to output and/or input audio signals. For example, the audio component may include a microphone, which is configured to receive external audio signals. The received audio signals may be further stored in the memory 1502 or transmitted through the communication component 1505. The audio component may further include at least one speaker for outputting audio signals.

The I/O interface 1504 provides an interface between the processor 1501 and other interface modules, which may include keyboards, mice, buttons, and the like. These buttons may be virtual buttons or physical buttons. The communication component 1505 is configured for wired or wireless communication between the electronic device 1500 and other devices. Wireless communication, such as Wi-Fi, Bluetooth, Near Field Communication (NFC), 2G, 3G, 4G, NB-IOT, eMTC, or other 5G, or a combination of one or more thereof is not limited here. Therefore, the corresponding communication component 1505 may include Wi-Fi module, Bluetooth module, NFC module, etc.

In an example embodiment, the electronic device 1500 may be implemented by one or more of Application Specific Integrated Circuit (ASIC), Digital Signal Processor (DSP), Digital Signal Processing Device (DSPD), Programmable Logic Device (PLD), Field Programmable Gate Array (FPGA), controller, microcontroller, microprocessor or other electronic components to perform the above multi-sequence scanning method.

In an example embodiment, a non-transitory computer-readable storage medium is coupled to at least one processor and stores programming instructions for execution by the at least one processor to perform the above multi-sequence scanning method. For example, the computer-readable storage medium may be the above memory 1502 storing a computer program, which may be executed by the processor 1501 of the electronic device 1500 to accomplish the above multi-sequence scanning method.

In an example embodiment, a computer program product includes a computer program executable by a programmable device. The computer program has a code portion for performing the above multi-sequence scanning method when executed by the programmable device.

In some examples, a CT system includes a ray source, a detector and the electronic device described above. The ray source is configured to emit rays. The detector is configured to detect an attenuated ray signal after the rays pass through a scanned object, convert the attenuated ray signal into an electrical signal, and send the electrical signal to the electronic device. The electronic device is configured to: in response to a parameter configuration command, configure scan sequence parameters for a plurality of scan sequences in a scan protocol to obtain a target scan protocol, where the scan sequence parameters include a scan start time and a scan duration of each of the scan sequences, and a scan switching duration between the scan sequences, a total scan duration of the scan sequences in the target scan protocol is configured to be less than or equal to a preset total scan duration, and the scan switching duration between the scan sequences is configured in a shortest duration mode; and in response to receiving a scan command, control the CT system to scan the scanned object according to the scan sequence parameters configured in the target scan protocol. In an example embodiment, the CT system may be shown in FIG. 10, which has been described above and will not be repeated here.

Some embodiments of the present disclosure have been described in detail above in conjunction with the accompanying drawings; however, the present disclosure is not limited to specific details in the above embodiments. A variety of simple modifications may be made to the embodiments of the present disclosure within the scope of the technical concept of the present disclosure, all of which fall within the protection scope of the present disclosure.

It should also be noted that various specific technical features described in the above specific embodiments may be combined in any suitable way without contradiction. In order to avoid unnecessary repetition, various possible combinations will not be described separately in the present disclosure.

Any combination of various embodiments in the present disclosure may also be possible, and as long as they do not contradict the idea of the present disclosure, they should be regarded as disclosed in the present disclosure.

The invention claimed is:

1. A multi-sequence scanning method for application in a CT system, the method comprising:
   in response to a parameter configuration command, configuring, by at least one processor, scan sequence parameters for a plurality of scan sequences in a scan protocol to obtain a target scan protocol, wherein each of the plurality of scan sequences corresponds to a respective scanned position of a scanned object, wherein the scan sequence parameters comprise a scan start time and a scan duration of each of the scan sequences, and a scan switching duration between the scan sequences, wherein a total scan duration of the scan sequences in the target scan protocol is configured to be less than or equal to a preset total scan duration, and wherein the scan switching duration between the scan sequences is configured in a shortest duration mode; and
   in response to receiving a scan command, controlling, by the at least one processor, the CT system to scan the scanned object according to the scan sequence parameters configured in the target scan protocol.

2. The method according to claim 1, wherein configuring the scan sequence parameters for the plurality of scan sequences in the scan protocol comprises:
   monitoring a scan peak time, wherein the scan peak time is the time when an average of CT values of a region of interest reaches a preset threshold, and the region of interest is a preset region where the CT values are to be monitored; and
   configuring the scan start time of the scan sequence covering the scan peak time according to the monitored scan peak time, such that the scan start time of the scan sequence is earlier than or concurrent with the scan peak time.

3. The method according to claim 1, wherein the scan sequences comprise a first scan sequence and a second scan sequence, and the first scan sequence is a previous scan sequence of the second scan sequence, and configuring the scan sequence parameters for the plurality of scan sequences in the scan protocol comprises:
   monitoring a scan peak time, wherein the scan peak time is the time when an average of CT values of a region of interest reaches a preset threshold, and the region of interest is a preset region where the CT values are to be monitored;
   configuring the scan start time of the second scan sequence according to the monitored scan peak time, such that the scan start time of the second scan sequence is earlier than or concurrent with the scan peak time; and
   adjusting the scan sequence parameters of the first scan sequence such that the time between the scan start time of the first scan sequence and the scan start time of the second scan sequence is equal to a sum of the scan duration of the first scan sequence and the scan switching duration, wherein the scan switching duration is the time to switch from the first scan sequence to the second scan sequence.

4. The method according to claim 3, wherein adjusting the scan sequence parameters of the first scan sequence comprises:
   adjusting the scan duration of the first scan sequence by adjusting a number of scan circles for the first scan sequence, a scan duration per scan circle for the first scan sequence, or both.

5. The method according to claim 3, wherein when the first scan sequence is the first one of the scan sequences, adjusting the scan sequence parameters of the first scan sequence comprises at least one of:
   adjusting the scan start time of the first scan sequence; or
   adjusting the scan duration of the first scan sequence by adjusting a number of scan circles for the first scan sequence, a scan duration per scan circle for the first scan sequence, or both.

6. The method according to claim 3, wherein adjusting the scan sequence parameters of the first scan sequence comprises:
   determining an actual scan end time of the first scan sequence according to an initial scan start time, an initial number of scan circles, and an initial scan duration per scan circle for the first scan sequence;
   obtaining a theoretical scan end time of the first scan sequence by subtracting the scan switching duration between the second scan sequence and the first scan sequence from the scan start time of the second scan sequence; and
   in response to the actual scan end time being inconsistent with the theoretical scan end time, adjusting the scan sequence parameters of the first scan sequence.

7. The method according to claim 3, wherein the scan sequences further comprise a third scan sequence, the third scan sequence is the next scan sequence of the second scan sequence, and the third scan sequence is the last one of the scan sequences, and wherein configuring the scan sequence parameters for the plurality of scan sequences in the scan protocol further comprises:
   adjusting scan sequence parameters of the third scan sequence such that the time between a scan end time of the third scan sequence and the scan start time of the first scan sequence is less than or equal to the preset total scan duration.

8. The method according to claim 1, wherein the parameter configuration command comprises one or more system operating parameters to be adjusted and values of the system operating parameters, and wherein the method further comprises, before configuring the scan sequence parameters for the plurality of scan sequences in the scan protocol:
   determining one or more target system operating parameters to be adjusted in synchronization with each of the system operating parameters to be adjusted, according to a parameter adjustment correlation and each of the system operating parameters to be adjusted, wherein the parameter adjustment correlation is configured to characterize a synchronous adjustment relationship between each of the system operating parameters to be adjusted and respective target system operating parameters; and adjusting values of the respective target system operating parameters according to the value of each of the system operating parameters to be adjusted.

9. A non-transitory computer-readable storage medium coupled to at least one processor and storing programming instructions for execution by the at least one processor to perform the method according to claim 1.

10. An electronic device, comprising:
at least one processor; and
one or more memories coupled to the at least one processor and storing programming instructions for execution by the at least one processor to perform operations comprising:
in response to a parameter configuration command, configuring scan sequence parameters for a plurality of scan sequences in a scan protocol to obtain a target scan protocol, wherein each of the plurality of scan sequences corresponds to a respective scanned position of a scanned object, wherein the scan sequence parameters comprise a scan start time and a scan duration of each of the scan sequences, and a scan switching duration between the scan sequences, wherein a total scan duration of the scan sequences in the target scan protocol is configured to be less than or equal to a preset total scan duration, and wherein the scan switching duration between the scan sequences is configured in a shortest duration mode; and
in response to receiving a scan command, controlling a CT system to scan the scanned object according to the scan sequence parameters configured in the target scan protocol.

11. The electronic device according to claim 10, wherein configuring the scan sequence parameters for the plurality of scan sequences in the scan protocol comprises:
monitoring a scan peak time, wherein the scan peak time is the time when an average of CT values of a region of interest reaches a preset threshold, and the region of interest is a preset region where the CT values are to be monitored; and
configuring the scan start time of the scan sequence covering the scan peak time according to the monitored scan peak time, such that the scan start time of the scan sequence is earlier than or concurrent with the scan peak time.

12. The electronic device according to claim 10, wherein the scan sequences comprise a first scan sequence and a second scan sequence, and the first scan sequence is a previous scan sequence of the second scan sequence, and configuring the scan sequence parameters for the plurality of scan sequences in the scan protocol comprises:
monitoring a scan peak time, wherein the scan peak time is the time when an average of CT values of a region of interest reaches a preset threshold, and the region of interest is a preset region where the CT values are to be monitored;
configuring the scan start time of the second scan sequence according to the monitored scan peak time, such that the scan start time of the second scan sequence is earlier than or concurrent with the scan peak time; and
adjusting the scan sequence parameters of the first scan sequence such that the time between the scan start time of the first scan sequence and the scan start time of the second scan sequence is equal to a sum of the scan duration of the first scan sequence and the scan switching duration, wherein the scan switching duration is the time to switch from the first scan sequence to the second scan sequence.

13. The electronic device according to claim 12, wherein adjusting the scan sequence parameters of the first scan sequence comprises:
adjusting the scan duration of the first scan sequence by adjusting a number of scan circles for the first scan sequence, a scan duration per scan circle for the first scan sequence, or both.

14. The electronic device according to claim 12, wherein when the first scan sequence is the first one of the scan sequences, adjusting the scan sequence parameters of the first scan sequence comprises at least one of:
adjusting the scan start time of the first scan sequence; or
adjusting the scan duration of the first scan sequence by adjusting a number of scan circles for the first scan sequence, a scan duration per scan circle for the first scan sequence, or both.

15. The electronic device according to claim 12, wherein adjusting the scan sequence parameters of the first scan sequence comprises:
determining an actual scan end time of the first scan sequence according to an initial scan start time, an initial number of scan circles, and an initial scan duration per scan circle for the first scan sequence;
obtaining a theoretical scan end time of the first scan sequence by subtracting the scan switching duration between the second scan sequence and the first scan sequence from the scan start time of the second scan sequence; and
in response to the actual scan end time being inconsistent with the theoretical scan end time, adjusting the scan sequence parameters of the first scan sequence.

16. The electronic device according to claim 12, wherein the scan sequences further comprise a third scan sequence, the third scan sequence is the next scan sequence of the second scan sequence, and the third scan sequence is the last one of the scan sequences, and wherein configuring the scan sequence parameters for the plurality of scan sequences in the scan protocol further comprises:
adjusting scan sequence parameters of the third scan sequence such that the time between a scan end time of the third scan sequence and the scan start time of the first scan sequence is less than or equal to the preset total scan duration.

17. The electronic device according to claim 10, wherein the parameter configuration command comprises one or more system operating parameters to be adjusted and values of the system operating parameters, and wherein the operations further comprise, before configuring the scan sequence parameters for the plurality of scan sequences in the scan protocol:
determining one or more target system operating parameters to be adjusted in synchronization with each of the system operating parameters to be adjusted, according to a parameter adjustment correlation and each of the system operating parameters to be adjusted, wherein the parameter adjustment correlation is configured to characterize a synchronous adjustment relationship between each of the system operating parameters to be adjusted and respective target system operating parameters; and adjusting values of the respective target system operating parameters according to the value of each of the system operating parameters to be adjusted.

18. A CT system, comprising:

a ray source;

a detector; and an electronic device, wherein:

the ray source is configured to emit rays;

the detector is configured to detect an attenuated ray signal after the rays pass through a scanned object, convert the attenuated ray signal into an electrical signal, and send the electrical signal to the electronic device; and the electronic device is configured to:

in response to a parameter configuration command, configure scan sequence parameters for a plurality of scan sequences in a scan protocol to obtain a target scan protocol, wherein each of the plurality of scan sequences corresponds to a respective scanned position of the scanned object, wherein the scan sequence parameters comprise a scan start time and a scan duration of each of the scan sequences, and a scan switching duration between the scan sequences, wherein a total scan duration of the scan sequences in the target scan protocol is configured to be less than or equal to a preset total scan duration, and wherein the scan switching duration between the scan sequences is configured in a shortest duration mode; and in response to receiving a scan command, control the CT system to scan the scanned object according to the scan sequence parameters configured in the target scan protocol.

* * * * *